(12) United States Patent
Krolman

(10) Patent No.: US 8,257,256 B1
(45) Date of Patent: Sep. 4, 2012

(54) RETRACTOR DEVICE

(76) Inventor: Arthur M. M. Krolman, Boston, MA (US)

( * ) Notice: Subject to any disclaimer, the term of this patent is extended or adjusted under 35 U.S.C. 154(b) by 111 days.

(21) Appl. No.: 12/910,422

(22) Filed: Oct. 22, 2010

Related U.S. Application Data

(60) Provisional application No. 61/253,919, filed on Oct. 22, 2009.

(51) Int. Cl.
 *A61B 1/32* (2006.01)
(52) U.S. Cl. ...................................................... 600/236
(58) Field of Classification Search ........... 600/184–246
 See application file for complete search history.

(56) References Cited

U.S. PATENT DOCUMENTS

| | | | |
|---|---|---|---|
| 1,230,873 A | 6/1917 | Crossley | |
| 1,375,445 A | 4/1921 | Crossley | |
| 2,438,646 A | 11/1945 | Puliam | |
| D151,651 S * | 11/1948 | Nield | D32/61 |
| 2,702,540 A | 7/1953 | Debeh | |
| 3,392,727 A * | 7/1968 | Hanlon | 606/210 |
| 3,616,497 A * | 11/1971 | Esposito, Jr. | 24/542 |
| 3,809,094 A * | 5/1974 | Cook | 606/151 |
| 3,906,957 A * | 9/1975 | Weston | 606/205 |
| 3,972,333 A * | 8/1976 | Leveen | 606/174 |
| D262,064 S * | 11/1981 | Rainin | D28/55 |
| 4,321,916 A | 3/1982 | McKee | |
| 4,356,821 A * | 11/1982 | Rind | 128/207.14 |
| 4,365,625 A * | 12/1982 | Rind | 128/207.14 |
| D309,809 S * | 8/1990 | Davidson | D32/61 |
| 5,002,561 A * | 3/1991 | Fisher | 606/210 |
| 5,070,860 A * | 12/1991 | Grounauer | 600/236 |
| 5,464,413 A * | 11/1995 | Siska et al. | 606/151 |
| 5,522,290 A * | 6/1996 | Visser et al. | 81/427 |
| 5,591,203 A * | 1/1997 | Fahy | 606/207 |
| 6,397,439 B1 * | 6/2002 | Langford | 24/518 |
| 6,440,065 B1 * | 8/2002 | Hered | 600/236 |
| 8,066,635 B2 * | 11/2011 | Beck | 600/236 |

OTHER PUBLICATIONS

Lid Speculum, http://www.mrcophth.com/ophthalmicinstruments/speculum/speculums.html, Oct. 22, 2010, 2 pages.

* cited by examiner

*Primary Examiner* — Alvin Stewart
*Assistant Examiner* — Mary Hoffman

(57) ABSTRACT

A retractor for ophthalmic procedures and other uses is disclosed. The retractor is a U-shaped body formed by two arms and a live hinge, with a retracting means at the distal end of each arm. The retracting means includes a tongue blade for insertion under an eyelid, a deflector for retracting the eyelid, and two ball-tipped posts that extend away from the tongue blade and prevent eyelid or eyelashes from obscuring the window opened up by the retractor. The hinge is also an adjustable biasing spring that biases the distal ends of the arms to an open position. Anti-torque arches are provided on the outer wall of the body. A brace may be provided on the retractor, to fix the device to a desired position.

13 Claims, 6 Drawing Sheets

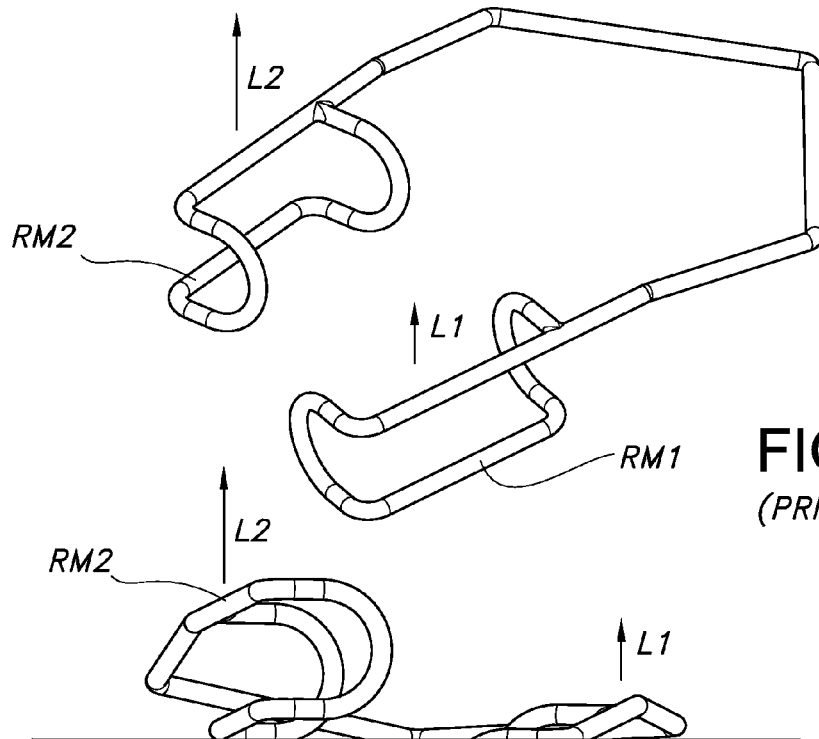
FIG. 8A
(PRIOR ART)
FIG. 8B
(PRIOR ART)
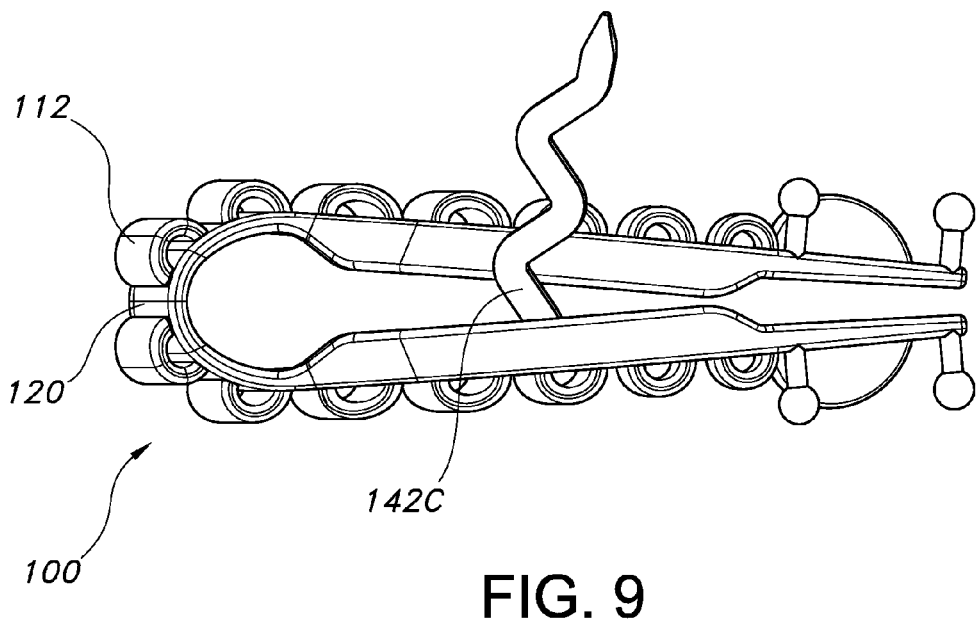
FIG. 9

RETRACTOR DEVICE

BACKGROUND INFORMATION

1. Field of the Invention

The invention relates to a retractor for holding an aperture open, and particularly an eyelid speculum.

2. Discussion of the Prior Art

A device referred to as an "eye speculum" or a "retractor" is frequently used for various medical procedures on the eye, to hold the upper and lower eyelids apart, in order to have access to the eye. Conventional eye specula include rigid, hinged metal devices, some withs an anti-close locking wheel to fix the speculum to a desired open position, as well as wire devices that have a live hinge, without any means for fixing the speculum to a particular open position.

Understandably, the hinged metal devices with the anti-close locking wheel are expensive to manufacture. They have multiple parts that require assembly, some of the parts require precision machining, etc. On the other hand, the wire devices with the live hinge can be difficult to use for a number of reasons. It is possible, for example, that when the two arms of the device are squeezed to bring the blades together for insertion under the eyelids, that the two arms become misaligned and, consequently, that a torque is exerted on the arms, causing the device to spring out from the operator's hand. The problem of a torque on the device also arises, when the pressures exerted on the respective blades by the upper and lower eyelids is very different.

Some conventional devices are not symmetrically constructed and, thus, a separate device must be used for the left eye and for the right eye. Some conventional devices have a solid upper blade, a shelf-like construction, for holding the eyelid open. Wire devices with a live hinge often have open wire blades with only two contact points retracting each lid. These constructions can create pressure points along the eyelid that cause discomfort to the patient, or damage the eyelid tissue and increase the risk of ptosis, commonly referred to as "droopy eyelid."

What is needed, therefore, is an eye speculum device that is inexpensive to manufacture and that is simple to use. What is further needed is such a device that applies a minimum amount of pressure to the patient's eye or eyelids, yet reliably holds the eyelid open. What is yet further needed is such a device that reduces the risk of pressure points along the patient's eyelid.

BRIEF SUMMARY OF THE INVENTION

The invention is a retractor device that is used to hold two sides of an opening apart. The initial intended use of the retractor is as an eye speculum that is used to hold the eyelids of a patient or a cadaver open, in order to provide a viewing or operating window, to enable ophthalmic procedures to be carried out on patients or to excise an eyeball or corneal disk from an eye donor. It is understood, however, that the device according to the invention is a retractor device that may be used in other types of medical procedures, on humans and animals, to hold open incisions in tissue, as well as a retractor device to hold apart many other types of materials, such as any type of flexible fabric. For purposes of illustration, reference is made below to the use of the retractor device as an eye speculum and a description of the features provided, relative to certain features of a patient's eye. This is not intended to be limiting, but merely to serve as a vehicle in the description of the inventive device.

The retractor device according to the invention is a single-piece construction of molded plastic. The single-piece construction is generally U- or V-shaped, formed by two arms connected by a live hinge that has a spring force/resistance. Disposed at each of the two free ends of the arms is a retraction means that includes a so-called "tongue blade" and means for deflecting and holding back tissue or flexible material from the window that the retractor device opens up. The two tongue blades or tongue tips together are insertable under an upper and a lower eyelid of a patient. The tongue blade may be curved to accommodate the curvature of the eyeball. The deflecting means includes a pair of ball-tipped posts provided at each free end of the two arms, the posts being spaced apart from each other and also spaced apart from the respective tongue blade and extending in an orientation substantially parallel to the tongue blade, to provide a retainer space for the eyelid, the tissue, or the material that is being held away from an area of interest.

When the retractor device is used as an eye speculum and inserted under the eyelids, each eyelid is constrained in the retainer space formed between the tongue blade and the posts. The spring force of the hinge holds the upper and lower eyelids apart. These posts are approximately the same height as the vertical dimension of the tongue blade. The posts have the advantage that they do not obstruct the operator's view of the tongue, while the retractor device is being inserted into position under the eyelid, as does the solid upper blade that is provided on many conventional devices. The ends of the posts have a ball tip or a knob to avoid uncomfortable pressure points in the patient's brow or cheek or to avoid contributing to the risk of ptosis or droopy lid. The retainer space also serves as an eyelash deflector, i.e., to hold the viewing or operating window free of eyelashes and to prevent the eyelashes from coming into contact with the eyeball.

A plurality of anti-torque arches are provided along the outer walls of the arms and the hinge. These arches serve to stiffen the device, yet allow flexibility at the live hinge. They also serve to increase the lateral stability of the two arms, that is, they prevent the arms from moving apart laterally relative to one another. For example, it is sometimes the case that the tissue below the eye is swollen and, as a result, exerts a greater force on the arm under the lower eyelid than the upper eyelid exerts on the arm under that eyelid. This force imbalance urges one of the arms to move in a lateral direction relative to the other arm. If unrestrained with regard to lateral movement, the unequal forces on the two arms may result in a torque on the retractor device that can be strong enough to flip the device out from under the eyelids, in which case, the wide operating window closes suddenly and unexpectedly. This may result in catastrophic failure of the ophthalmic procedure. In the embodiment designed as an eye speculum, the retainer space, i.e., the eyelash deflector, extends up to 112 mm outward at a right angle to the arms, to provide sufficient space to accommodate the eyelid. Pressure from the eyelids against the eyelash deflectors exerts a torque on the arms of the retractor device. Several features of the inventive device counteract this torque. The spring hinge applies a force against the eyelash deflectors, to hold open the operating window. The anti-torque arches nearest the tongue blade serve to counteract the torque exerted by the eyelids. In the absence of these anti-torque arches, the opposing eyelash deflectors would twist inward toward one another and, as the more upright tongue blade edge scraped the eyeball, the speculum would be rejected. This, too, could result in catastrophic failure of the ophthalmic procedure. Finally, the plurality of arches serves as an ergonomic grip that allows the surgeon to compress the eye speculum for insertion, without it sliding out from between the fingers and without the fingers slipping down toward the blades.

The live hinge of the retractor device according to the invention provides sufficient force to hold the eyelids apart. Depending on the intended use of the device according to the invention, however, it may be desirable to include means for bracing the retractor device open. A bracing leg and positioning means may be incorporated into the device, for example, on the inside walls of the two arms. It may sometimes be necessary to secure the retractor device to an open position. For example, the forces exerted by the material being held apart by device may be strong enough to urge the device toward a closed position. Using the device as an eye speculum, this can sometimes be the case with cadaver lids, when a technician requires a very wide operating window in order to excise a donor corneal disk greater than 18 mm diameter. Such large diameter disks are required for subsequent placement on an artificial chamber for preparation of endothelial keratoplasty grafts, for example. The brace means counteracts these forces and holds the eye speculum open to the desired position. The proximal end of a bracing leg is disposed on the inner wall of one arm and a series of ridges provided on the inner wall of the opposite arm. The distal end of the bracing leg may be snapped into position between any two adjacent ridges. This prevents the pressure from the eyelids from moving the arms of the speculum closer together, and thus, allowing the eyelids to close. The eye speculum may be held open to a greater or lesser degree, depending on where in the series of ridges the end of the bracing leg is snapped into place. The closer the bracing leg is secured toward the hinge, the wider the device is urged open.

As mentioned above, the live hinge provides sufficient force for many applications, including that as an eye speculum, to hold the retraction means apart without the need for any bracing leg. In some cases, the initial force exerted by live hinge may be excessive for the particular procedure or patient. For example, an elderly patient with delicate lids, who, in the estimation of the operator, does not have the determination or physical ability to voluntarily force his or her lids shut against the force of the device, may require a lesser force to maintain the lids in a retracted position. The construction of the live hinge of the retractor device according to the invention provides a biasing spring that is infinitely variable in force reduction, such that force exerted on the retraction means by the hinge may be adapted to the specific application. This is accomplished by the operator simply squeezing the live hinge near the hinge apex until the plastic weakens to the desired force level.

BRIEF DESCRIPTION OF THE DRAWINGS

The present invention is described with reference to the accompanying drawings. In the drawings, like reference numbers indicate identical or functionally similar elements. The drawings are not drawn to scale.

FIG. 8A is a perspective view of a conventional wire eye speculum, illustrating lateral instability of the two arms.

FIG. 8B is a front view of the eye speculum of FIG. 8A, illustrating lateral instability.

FIG. 9 shows how to reduce the biasing spring force of the live hinge.

DETAILED DESCRIPTION OF THE INVENTION

The present invention will now be described more fully in detail with reference to the accompanying drawings, in which the preferred embodiments of the invention are shown. This invention should not, however, be construed as limited to the embodiments set forth herein; rather, they are provided so that this disclosure will be complete and will fully convey the scope of the invention to those skilled in the art.

Figure 1:
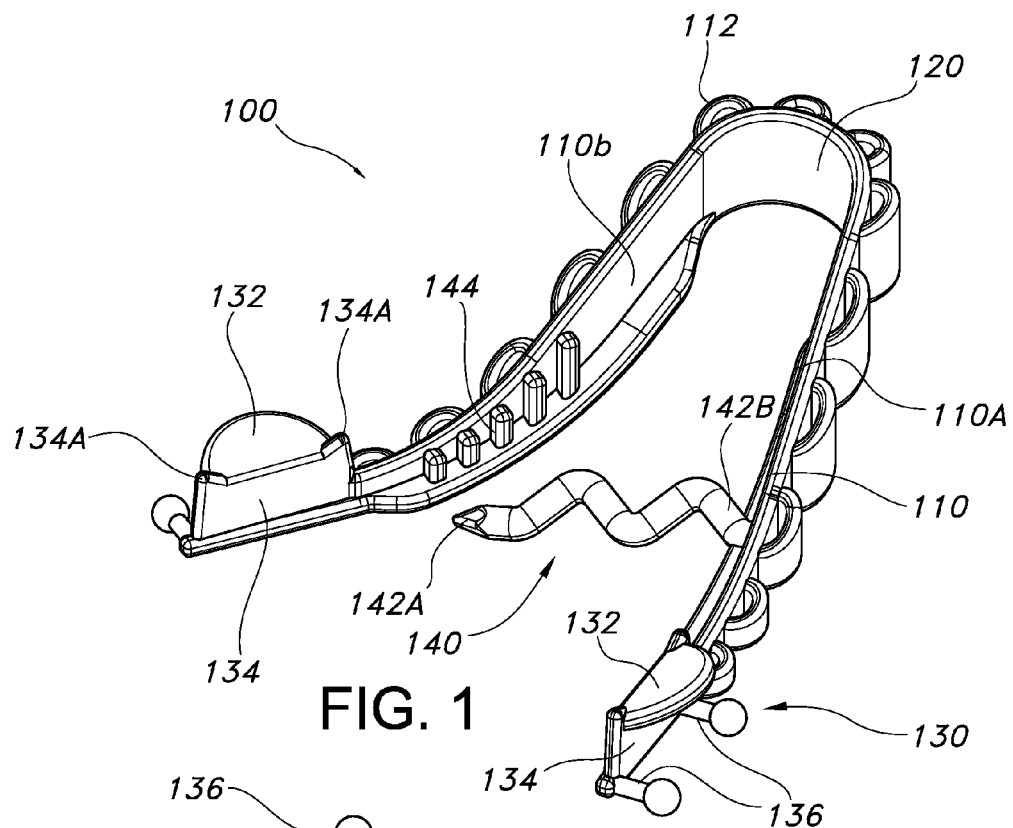
FIG. 1 is a perspective view of a first embodiment of the eye speculum according to the invention, showing the rear side and illustrating particularly the bracing leg and the positioning means.
Figure 10:
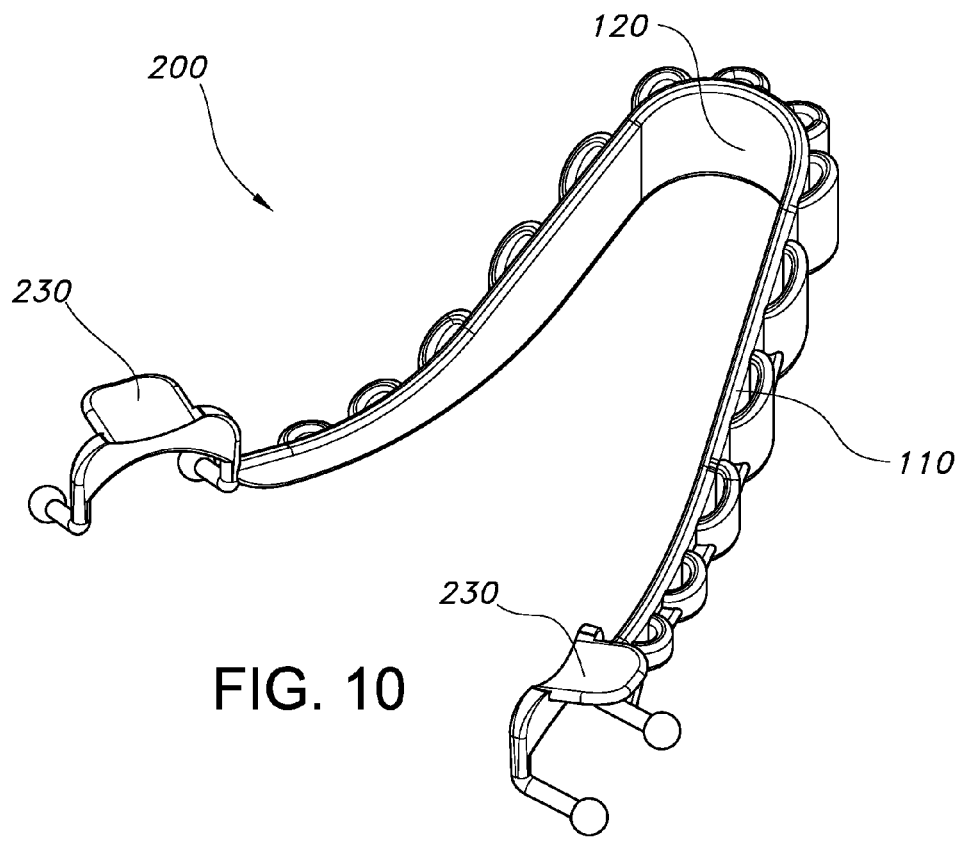
FIG. 10 is a perspective view of a second embodiment of the retractor device according to the invention.
Figure 11:
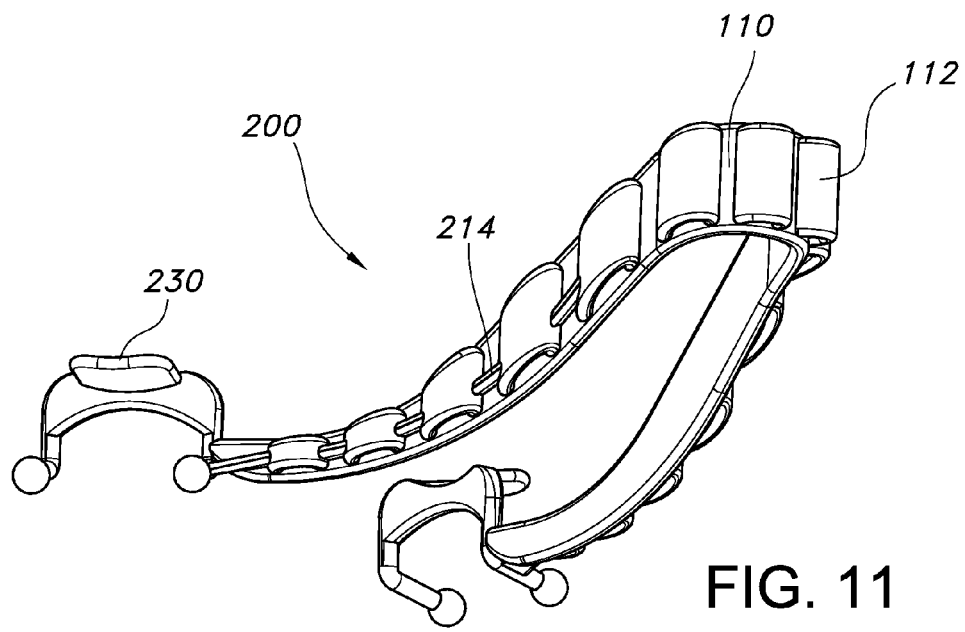
FIG. 11 shows stiffening fins between the anti-torque arches.
Figure 12:
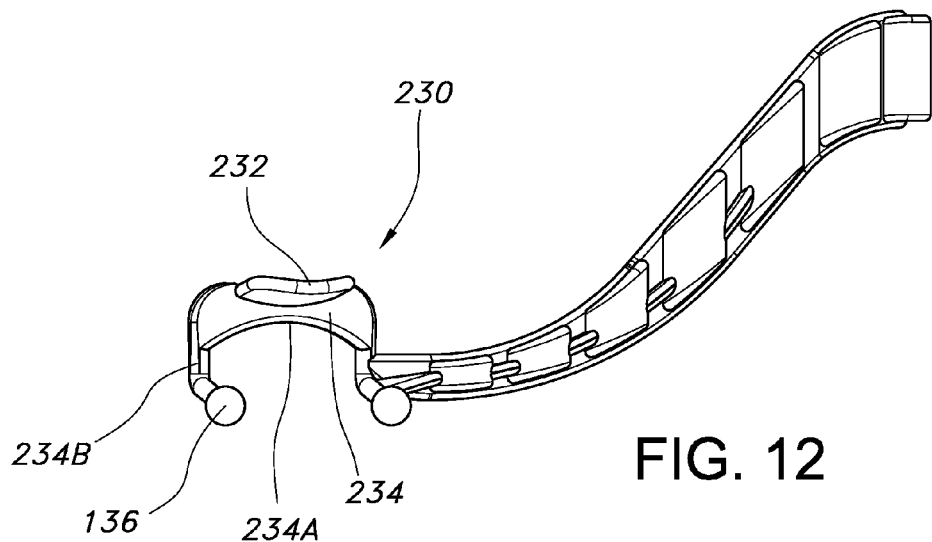
FIG. 12 shows the curved contours on the deflector.
Figure 13:
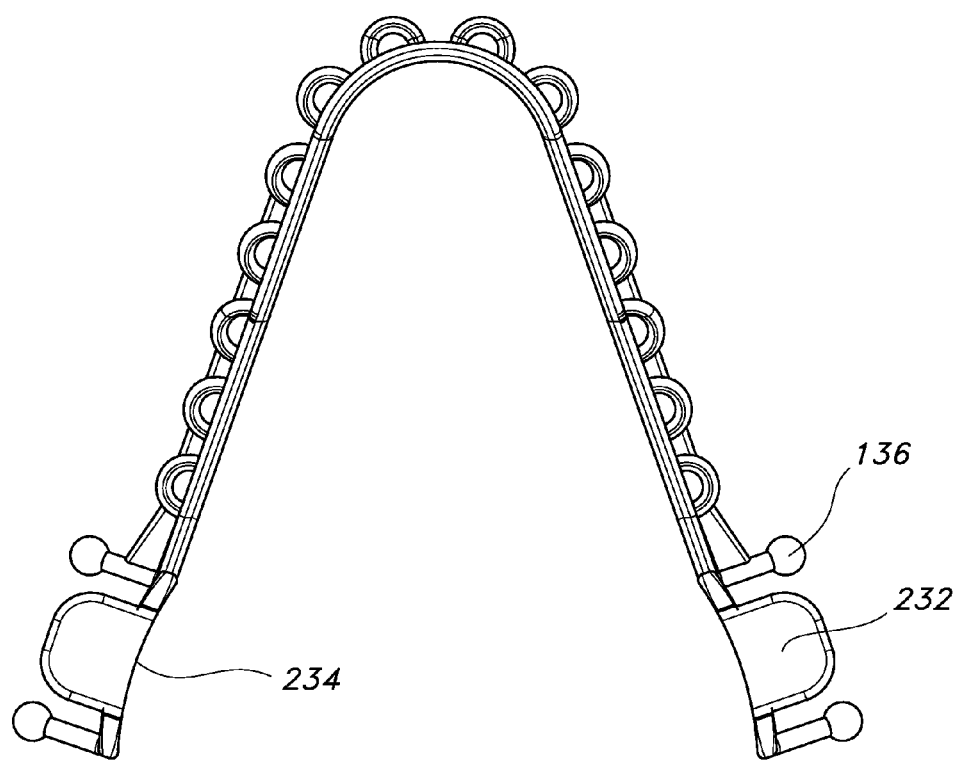
FIG. 13 shows the curved tongue blade of the device.

FIGS. 1 and 10 show perspective views of two embodiments of a retractor device according to the invention. The first embodiment is a retractor device 100 with a bracing means and the second a retractor device 200 without bracing means. Common to both embodiments 100 and 200 is a single-piece molded construction that provides economic advantage as well as improved functional design over conventional retractor devices.

FIGS. 2-9 illustrate various features of the first embodiment retractor device 100. The retractor device 100 has an overall U- or V-shape and is a unitary molded piece comprising a pair of arms 110, a hinge 120, retraction means 130, and anti-close brace means 140, whereby all of the elements 110-140 are integrated into the molded construction of the piece.

The pair of arms 110 include arms 110A and 110B. Each arm 110A, 110B terminates at its respective distal or free end in the retraction means 130; the opposite ends of the arms 110A, 110B are joined together by the live hinge 120 that also functions as a biasing spring, to bias the retractor device 100 to an open position, that is, to keep the retraction means 130 spread apart from each other. Anti-torque or stiffening arches 112 are provided on the outer wall of the arms 110 and the hinge 120. The anti-torque arches 112 may be spaced closer together along the arm sections 110A and 110B and somewhat farther apart at the hinge 120. In the embodiment shown, the anti-torque arches 112 are hollow curved walls that are formed on the outer surface of the arms. These arches 112 serve multiple functions: on the one hand, they function as a biasing spring at hinge 120 that biases the distal ends of the arms 110 with the retraction means 130 apart and, on the other hand, provide the hinge 120 with enough flexibility, so that the arms 110 may be urged toward each other against the spring force of the hinge 120. The anti-torque arches 112 nearest the tissue retraction means 130 serve to counter any torque exerted against the retraction means 130 and to improve lateral stability of the arms 110. The shape of the anti-torque arches 112 makes the arms 110 highly resistant to moving in a lateral direction. Lateral stability is discussed below with reference to FIGS. 8A and 8B. A further advantage of the anti-torque arches 112 is that they provide enhanced grippability for the surgeon, because the uneven surface of the arches improves the grip of the fingers on the arms 110 when squeezing the retractor device 100 for insertion.

Figure 3:
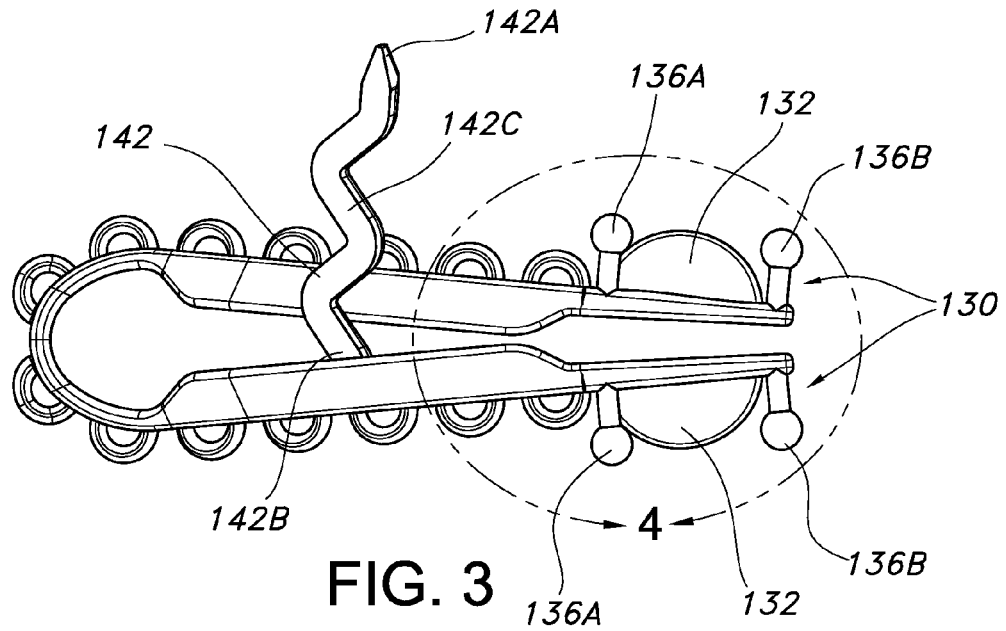
FIG. 3 is a side view of the eye speculum, showing the tissue retraction means of each arm brought together, for insertion under eyelids.
Figure 4:
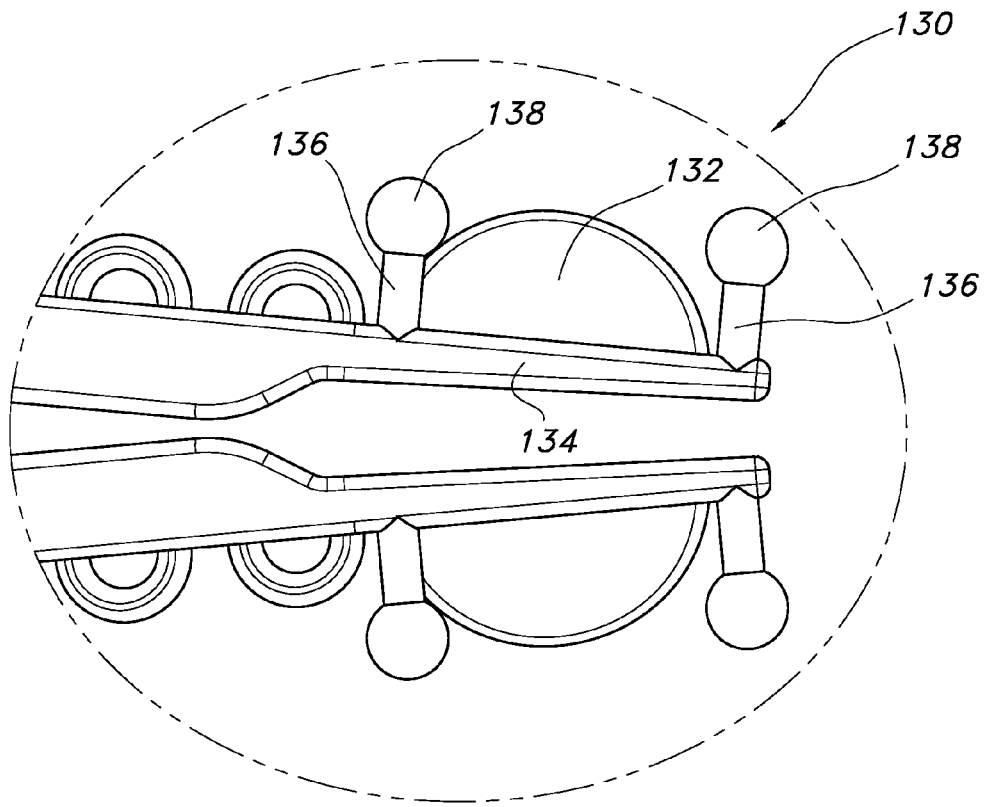
FIG. 4 is a close view of the tissue retraction means, showing the tongue blade, the eyelash deflector with adjacent anti-torque arches, and the ball-tipped posts.
Figure 5:
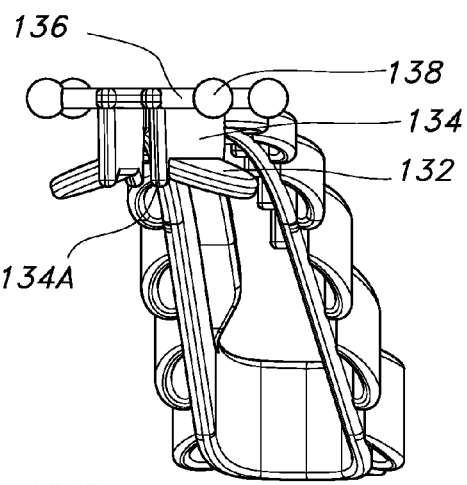
FIG. 5 is a perspective view of the tissue retraction means, to show particularly the eyelash deflector.

FIGS. 3-6 illustrate the details of the retraction means 130, which includes a tongue blade 132 that is insertable under an the object to be force apart, a deflector 134, and retainer posts 136. Remaining with the example of an eye speculum as an illustration vehicle, whereby the object to be forced apart is an eyelid, the deflector 134 provides a space for the displaced eyelid that is being forced open and the retainer posts 136, as mentioned above, assist in counteracting the torque exerted by the eyelids. The retainer posts 136 extend outward from the tongue blade 132. Pressure from the eyelid would cause the posts 136 to twist. If the pressure from the eyelid is great enough, it may be sufficient to normally overcome the counteracting force exerted by the anti-torque arches 112 closest to the tongue blade 132. The posts 136 are sufficiently long so that the ball tips will be forced against the brow or cheek of the patient. The brow or the cheek of the patient, then, effectively transmits a greater counteracting anti-torque force to the retainer posts 136, thereby maintaining proper orientation of the retainer posts 136 and, thus, of the tongue blade 132. FIG. 3 shows the retainers 136 as a pair of posts 136A and 136B. In this first embodiment, the deflector 134 is formed as a horizontal shelf relative to the vertical dimension of the tongue blade 132, with the tongue blade 132 formed on the inner edge and the retainers 136A and 136B formed on the outer edge of the deflector 134. The ends of the pair of posts 136 are formed as ball tips 138, as best seen in FIGS. 4 and 5. The edge of the deflector 134 that comes into contact with the eyeball has a curved contour formed by two protrusions 134A with a center portion 134B therebetween. Compared to the deflector 234 of embodiment 200, described below, the deflector 134 serves to hold eyelashes more securely out of the viewing/operating window. The rounded contour ensures that eyelashes don't have an opportunity to protrude into the operating window through openings resulting from a mismatch of the contour of the deflector 134 and the contour of the eyeball. This is important, because the eyelashes are a possible source of bacterial contamination.

Figure 6:
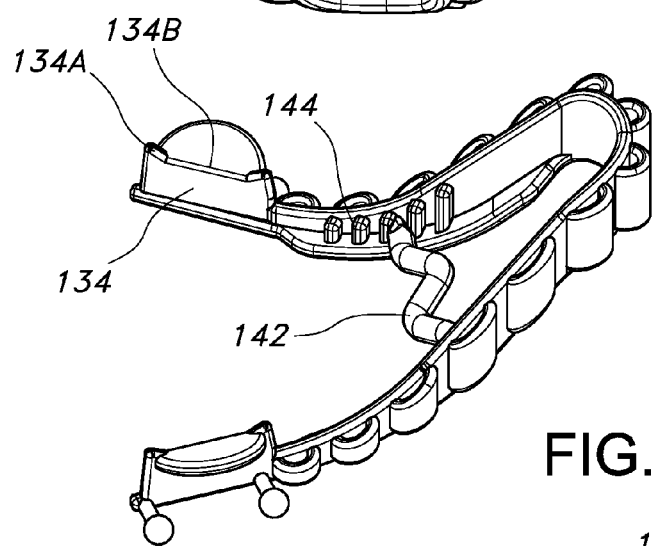
FIG. 6 illustrates the distal end of the bracing leg being secured at a particular location in the positioning means.

FIGS. 1 2, 3, and 6 illustrate features of the anti-close brace means 140, which includes a positioning means 144 and a bracing leg 142. In the embodiment shown, a series of ridges or stops serve as the positioning means 144. The bracing leg 142 has a proximal end 142B and a distal end 142A. The distal end 142A of the bracing leg 142 may be pushed over the positioning means 144 until the leg 142 catches in a recess between ridges at the desired position, as shown in FIG. 6. This holds the arms 110 of the retractor device 100 to a desired open position. Securing the distal end 142A closer to the hinge 120 widens the opening.

In the embodiment shown, the bracing leg 142 is constructed as a "wavy stick" which provides the desired flexibility to move the distal end 142A into the positioning means 144 and also the desired stiffness for use as a brace. The rear side of the bracing leg 142 has a groove 142C that extends most of the length of the leg shown in FIGS. 3 and 9. The inventor discovered that the combination of the waviness and the groove in the bracing leg 142 provides much improved characteristics compared to a conventional bracing means. The waviness improves the bending strength and the reliability of the bracing leg. Bending occurs along the length of the bracing leg and particularly, at the curved sections. This reduces the stresses that would normally be concentrated at the proximal end and, thus, reduces the likelihood that the bracing leg will fail. The groove 142C and the curves enable a controlled compression of the bracing leg 142 when positioning the distal end 142A. A further advantage of the waviness of the bracing leg 142 is that it provides a blocking means for the finger of the surgeon or technician. As shown in FIG. 3, the bracing leg 142 extends upward along the outside of the opposite arm 110 during the insertion process and naturally acts as a guard to keep fingers away from the opening.

FIGS. 10-13 illustrate a simplified, second embodiment of a retractor device 200 according to the invention. This second embodiment is very similar in concept to the first embodiment, but the anti-close brace means 140 have been eliminated and the retraction means modified to a retraction means 230 that provides certain advantages for the use of the retractor device 200 as an eye speculum. The arms 110, the live hinge 120, and the anti-torque arches 112 remain essentially the same. The retraction means 230 has a tongue blade 232 that is curved, the curvature corresponding to the shape of the typical eyeball. A deflector 234 has a curved contour 234A on the edge that extends between the ball tipped posts 136. This curve 234A allows the operator easier access to the eyeball, in other words, allows the operator to approach the eyeball more obliquely from the direction of the patient's brow. This is particularly useful, when the operator is using a tool, for example, forceps or a phacoemulsification probe, such as is used in cataract surgery. Although the curve 234A may hold eyelashes back less securely than the deflector 134, described above, this will normally not be an issue, because a plastic or vinyl drape is typically used for most surgical procedures. The drape is a sheet that is placed over the patient's head, with about a 1.5 inch diameter hole that is aligned over the patient's eye. When using the eye speculum in a surgical procedure, the operator tucks the drape over the eyelids first and then puts the eye speculum in place. The blades of the eye speculum blades thus hold back the patient's lids wrapped inside the drape, which prevents the eyelids and, particularly, the eyelashes from infecting the surgical area. Furthermore, the triangular shaped deflector wall that extends between each ball-tipped post and the tongue blade is sufficiently large to hold eyelashes away from the surgical area, even without use of a drape. Stiffening fins 214 are provided as bridges between adjacent anti-torque arches 112, to enhance lateral stability of the arms 112.

Figure 7:
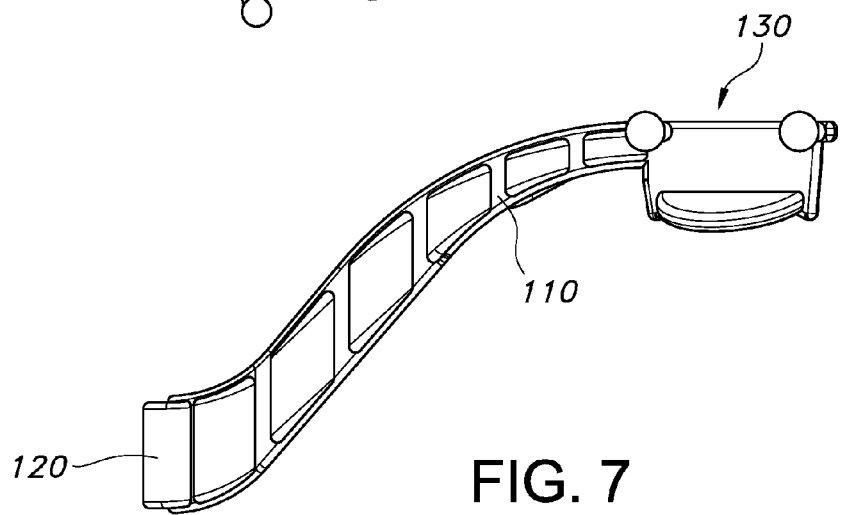
FIG. 7 is a side plane view of the eye speculum, illustrating a curvature of the arms that corresponds to the shape of the human adult cranium.

Use of the Retractor as an Eye Speculum: The retractor devices 100/200 may be used to hold the eyelids of a patient or eye donor far apart, to provide a viewing window for an ophthalmic procedure, or to excise an eyeball. The retractor device 100/200 has two arms 110 with retraction means 130/230 that mirror each other about a longitudinal axis. The device 100/200 may thus be used to open up the right or left eye. When inserted to maintain a viewing or operating window, the retraction means 130/230 are closer to the nose, with the hinge 120 extending out toward the outer edge of the head. The retractor device 100 has an overall profile in the side view that approximates the curvature of the average adult cranium, that is, the arms 110 are curved backward, away from the plane of the retraction means 130/230. This curvature places the hinge 20 of the device away from the working area of the ophthalmologist. FIG. 7 illustrates the offset location of the hinge end of the device, relative to the retraction means.

Figure 2:
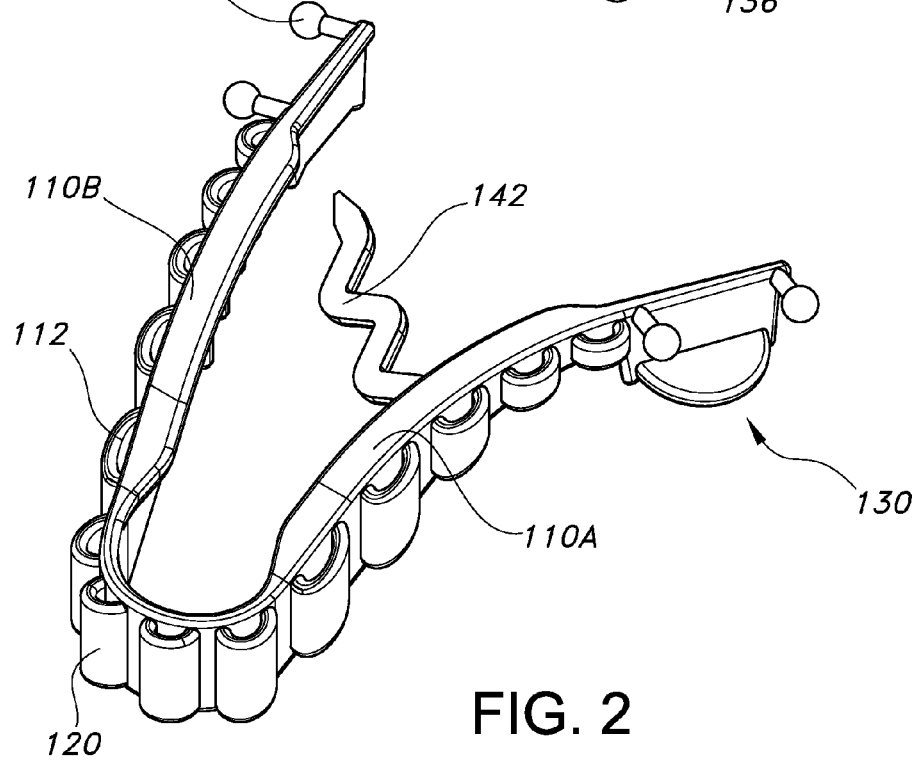
FIG. 2 is a perspective view of the eye speculum of FIG. 1, showing the front side and illustrating particularly the stiffening arches on the outer wall of the device.

The terms "upper" and "lower", as used to designate the arms 110, are relative terms, depending on whether the retractor device 100/200 is being inserted in the right or left eye. In other words, the arm 110A as shown in FIGS. 1 and 2 is an upper arm when the device is inserted into the left eye of a person and a lower arm when inserted into the right eye. The arms 110 are squeezed together to bring the retraction means 130 on each arm close to the other, as shown in FIG. 3. The tongue blade 132 of the upper arm is inserted under the upper eyelid and the tongue blade 132 of the lower arm inserted under the lower eyelid. The retainer posts 136A and 136B provide the advantage that they do not obscure the greatest part of the window or restrict unnecessarily the angle of insertion during the insertion step. The area of insertion is further increased in the second embodiment, with the curved geometry of the deflector 234. This improves the ability of the surgeon or technician to visually control the insertion step at all times.

In certain applications, it may be necessary to reduce the spring bias of the hinge 120. This is done by squeezing the arms close together near the hinge 120, as shown in FIG. 9. The construction of the live hinge 120 with the anti-torque arches 112 around it, allows the tension exerted by the hinge 120 to be weakened, without causing the hinge to fail. The retractor device 100/200 is intended to be used once and then discarded. Thus, it is a particular advantage of the device according to the invention that the hinge force can be easily adjusted on site, manually, to accommodate the individual application.

FIGS. 8A and 8B illustrate a condition of lateral instability on a conventional wire eye speculum. This is a condition that occurs when the arms 110 deflect laterally, relative to one another. This is often caused by the fact that the tissue on one side of the eye, i.e., above or below the eye, is swollen. For example, the facial tissue below the eye, on the cheek side, is swollen. Assuming the patient is lying on his back, facing upward, the pressure from the cheek exerts a greater lateral or upward force on the retraction means RM1, than the tissue on the brow side exerts on the retraction means RM2. The arrows L1 and L2 represent the magnitude of force exerted on the respective retraction means. A horizontal line is drawn through the image of the prior art device in FIG. 8B. "Lateral deflection" refers to a difference in height between the two retraction means RM1 and RM2 relative to that horizontal place. As shown, the greater force L2 forces the retraction means RM2 upward to a greater degree than the force L1. This lateral instability may create a torquing force on the device, which may result in the eye speculum moving out of position, and sometimes, even flipping out from under the eyelids. When this happens, the eyelids may suddenly snap shut in the middle of a delicate procedure on the eye. The anti-torque arches 112 embodied in the retractor devices 100/200, and particularly the anti-torque arches 112 with the stiffening fins 214, serve to promote strong lateral stability of the arms 110 and, thus, to prevent the retractor device 100/200 from changing position unexpectedly. The shape of the anti-torque arches 112 is of a half hollow cylinder. Other shapes, hollow or solid, may also be suitable, but this cylindrical shape is particularly suited to increase a resistance in the arms 110 to move in a lateral direction, i.e., to improve the lateral stability of the device.

Once the retractor device 100 is properly positioned, the distal end 142A of the brace 142 may be moved across the positioning means or series of stops 144 until it snaps into a recess between stops 144 at a desired open position, shown in FIG. 6.

The retractor devices 100 and 200 are preferably made of a molded thermoplastic material and most preferably, of acetal polymer, a thermoplastic that is known for its high rigidity without brittleness, high strength, resistance to fatigue, and lubricity. One advantage of this material is that it can withstand the severe stresses when the hinge is squeezed hard, without breaking. The crystalline structure of the material changes under the stress and this results in the desired weakened hinge. The lubricity of acetal feels comfortable against the skin or eyelid of the patient when the device is inserted. The entire retractor device 100/200 has no sharp edges that will damage sutures possibly used by a surgeon. The tongue blade is rounded and the edge blunt enough that it will not traumatize the delicate palpebral conjunctiva tissue it comes into contact with inside the surface of the eyelid.

It is understood that the embodiments described herein are merely illustrative of the present invention. Variations in the construction of the eye speculum may be contemplated by one skilled in the art without limiting the intended scope of the invention herein disclosed and as defined by the following claims.

The invention claimed is:

1. A retractor device for holding open two sides of a flexible material that bounds an aperture, so as to provide a viewing window between the two sides of the flexible material, the retractor device comprising:
   a U-shaped body, constructed as a single unitary piece of a formable plastic material, the U-shaped body including a live hinge and two arms, a proximal end of each arm joined by the hinge;
   a series of anti-torque arches disposed along an outer wall of the two arms and the live hinge, the anti-torque arches serving to enhance lateral stability of the two arms and to control a spring force at the hinge; and
   a retracting means provided at a distal end of each arm, the retracting means including a tongue blade for insertion under the flexible material and a deflector connected to and extending orthogonally from the tongue blade for restraining the flexible material to an open position.

2. The retractor device of claim 1, wherein the live hinge serves as a biasing spring to bias the retracting means to a normally open position.

3. The retractor device of claim 2, wherein the live hinge has a resilience and flexibility that allows a force reduction of the biasing spring by squeezing together the two arms in proximity to the live hinge, so as to reduce the force exerted by the live hinge on the retraction means.

4. The retractor device of claim 3, wherein the force reduction is infinitely variable.

5. The retractor device of claim 1, wherein the deflector has a first edge that adjoins the tongue blade and a second edge spaced a distance from the first edge, and wherein the deflector further includes a pair of retainer posts that extend from the second edge, in a direction parallel to the tongue blade, the retainer posts serving to hold the flexible material away from the aperture.

6. The retractor device of claim 5, wherein the retainer posts have rounded tips.

7. The retractor device of claim 1, wherein the anti-torque arches have a half-cylindrical form.

8. The retractor device of claim 1, wherein the anti-torque arches are hollow.

9. The retractor device of claim 1, wherein a stiffening fin is provided as a bridge between adjacent anti-torque arches.

10. The retractor device of claim 1, the U-shaped body further including an anti-close brace that includes a bracing leg that is joined at a proximal end to an inner wall of a first one of the two arms and a positioning means that is provided on an inner wall of a second one of the two arms for, wherein a distal end of the bracing leg is restrainable at a selected position along the positioning means.

11. The retractor device of claim 10, wherein the positioning means is a series of ridges and the distal end of the bracing leg is restrainable in a groove between two adjacent ridges.

12. The retractor device of claim 10, wherein the bracing leg has at least one S-shaped curve between the distal end and the proximal end.

13. The retractor device of claim 10, wherein the bracing leg has a groove along one side of the leg, to enhance flexibility of the bracing leg.

* * * * *